United States Patent [19]

Molina

[11] 4,392,982

[45] Jul. 12, 1983

[54] EXTENDED BIODEGRADABLE DYE PENETRANT COMPOSITION

[75] Inventor: Orlando G. Molina, Westminster, Calif.

[73] Assignee: Rockwell International Corporation, El Segundo, Calif.

[21] Appl. No.: 247,183

[22] Filed: Mar. 24, 1981

[51] Int. Cl.³ .................. G01N 21/88; C09C 3/00; B01N 33/00
[52] U.S. Cl. .................. 252/408.1; 252/301.19; 252/960; 73/104; 250/302
[58] Field of Search .................. 252/408, 301.19; 73/104

[56] References Cited

U.S. PATENT DOCUMENTS

| | | | |
|---|---|---|---|
| 2,870,220 | 1/1959 | Carter | 260/615 |
| 3,429,826 | 2/1969 | Alburger | 252/301.2 |
| 3,838,160 | 9/1974 | Molina | 252/408 |
| 3,915,885 | 10/1975 | Molina | 252/301.2 |
| 3,915,886 | 10/1975 | Molina | 252/301.2 P |
| 3,939,092 | 2/1976 | Molina | 252/301.2 P |
| 4,054,535 | 10/1977 | Molina | 73/104 |
| 4,160,375 | 7/1979 | Brittain et al. | 73/104 |
| 4,186,304 | 1/1980 | Molina | 250/302 |
| 4,191,048 | 3/1980 | Molina | 73/104 |

*Primary Examiner*—Benjamin R. Padgett
*Assistant Examiner*—M. Moskowitz
*Attorney, Agent, or Firm*—Charles T. Silberberg; Max Geldin

[57] ABSTRACT

A liquid dye penetrant composition for use in non-destructive testing of objects to locate cracks and other defects or flaws therein, said composition comprising (1) a nonionic surfactant, such as an oxyalkylated aliphatic alcohol, (2) a small amount of a dye soluble in the surfactant and (3) a substantial and preferably a major proportion, of an N-alkyl-2-pyrrolidone, preferably N-methyl-2-pyrrolidone, as extender. Such composition is applied to the surface of an object containing cracks and other defects, water is applied to the surface of the object to remove excess liquid dye penetrant composition from the surface without removing such penetrant from such cracks and other defects, and with or without a developer, the surface of the object is viewed under suitable lighting conditions, e.g. ultraviolet or black light when the dye in the penetrant is a fluorescent dye to locate any cracks or other defects in the surface of the body as indicated by colored traces from the dye penetrant remaining in such cracks and other defects.

17 Claims, No Drawings

EXTENDED BIODEGRADABLE DYE PENETRANT COMPOSITION

BACKGROUND OF THE INVENTION

This invention relates to an improved dye penetrant composition for non-destructively testing materials to locate defects open to the surface, such as cracks, and is more particularly concerned with the provision of a biodegradable dye penetrant composition which is extended with a biodegradable extender which is compatible with the liquid vehicle of the dye penetrant, is highly water soluble, and is an excellent solvent for dyes and surfactants used in dye penetrant formulations, as well as possessing other important characteristics such as low viscosity, low volatility, quick penetration into cracks and voids, low toxicity, and low metal corrosion.

In known penetrant inspection methods for rapid location and evaluation of surface flaws such as cracks in test bodies or parts, a dye penetrant composition, preferably containing a fluorescent dye, and which will penetrate the openings of the surface of cracks or other voids in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks, to be drawn up out of the surface defects by capillary action. The part is then exposed to appropriate lighting conditions such as invisible fluorescigenous light, and the location of the surface cracks is revealed by the emmission of visible fluorescent light by the penetrant dye which was retained in the cracks after the penetrant composition was removed from the surface of the part.

For best efficiency, particularly for the detection and location of minute surface cracks, as well as intermediate size and gross cracks, it is necessary that the dye penetrant composition have high sensitivity.

Volatile type solvents are commonly employed for extending or thinning dye penetrant inspection solutions or compositions. This is done chiefly for the purpose of lowering the viscosity of the penetrant in order to adapt it for application in spraying systems. Thus for example solvents such as kerosene, light fuel oils, light mineral oil, mineral thinner and methyl ethyl ketone, all highly volatile solvents, have heretofore been employed in prior art dye penetrants. See for example U.S. Pat. Nos. 2,806,959 and 3,429,826. Further, most dye penetrant solutions in practice generally require the use of a combination of solvents, including primary and secondary solvents, extender solvents and wetting agents.

Further, with the advent of new alloys employed in aircraft construction, such as titanium and nickel alloys, considerable effort has been made in selecting solvents which can be compatible with such alloys. Solvents compatible with these alloys generally are selected because of their unusually low chloride content and low sulfur content.

However, the use of volatile solvents in dye penetrant compositions has certain disadvantages. Thus, the use of a volatile solvent in dye penetrants results in the evolution of fumes and solvent vapors which are rapidly formed by the evaporating solvent. Also, when such solvents evaporate, the performance of such penetrants radically changes by changing the washability and sensitivity of the penetrants.

An additional criterion has recently developed also with respect to dye penetrant solutions and compositions. Generally, dye penetrant solutions presently being used and containing solvents and wetting agents present a disposal problem and hence the necessity for the development of dye penetrant solutions and compositions which are biodegradable, that is which employ dye solvents and carriers which are biodegradable, and are readily available despite the petrochemical shortage, has attained considerable importance. At present water pollution laws are becoming more and more strict with respect to the amount of pollutants which can be discarded into sewers and waterways.

Accordingly, in my Patent Nos. 3,915,884 and 3,915,886 there are disclosed water washable biodegradable dye penetrant compositions containing as primary vehicle for the dye, certain nonionic aliphatic oxyalkylated alcohol surfactants, preferably in the form of mixtures thereof.

However, biodegradable penetrants, e.g. those noted in the last two mentioned patents and which contain as primary vehicle the above noted surfactants, have relatively high viscosity. The result is that there is a high "drag out" loss when parts dipped into the dye penetrant solution, as is often done in practice, are removed from the solution. Such "drag out" loss is due to an entrapment of excess penetrant on the parts.

Further, due to the high viscosity of such biodegradable dye penetrant compositions, when such compositions are employed in spraying systems such as electrostatic spraying, the addition of conventional organic solvents such as those noted above for thinning purposes, essentially destroys the biodegradability of the resulting solvent extended penetrant, and/or tends to produce toxic fumes, or increases the flammability, thus defeating the use and advantages gained by employment of an initially biodegradable dye penetrant.

My U.S. Pat. No. 4,186,304 discloses a liquid dye penetrant composition comprising an oxalkylated aliphatic alcohol nonionic surfactant of the types described in the aforementioned U.S. Pat. Nos. 3,915,885 and 3,915,886, and containing as an extender the high boiling narrow-cut isoparaffins having a chain length of about 10 to about 17 carbon atoms. Although the use of such isoparaffinic solvent extender has certain important advantages, including high flash point, low volatility, absence of odor and provides a dye penetrant of low viscosity, the incorporation of such organic solvent in the oxyalkylated aliphatic alcohol surfactant employed as vehicle in the dye penetrant, has the disadvantage of rendering the resulting dye penetrant nonbiodegradable.

My U.S. Pat. No. 3,838,160 discloses that pyrrolidones have been used as a primary vehicle in dye penetrant compositions. The patent discloses also that in such compositions, secondary solvents such as certain ketones can be employed, e.g. isobutyl heptyl ketone. Also there can be incorporated into such dye penetrant composition containing pyrrolidones as primary vehicle, certain water soluble and water insoluble surfactants, such as a nonyl phenyl ether of polyethylene glycol. It is noted that such surfactants are generally used in substantially larger amounts than the primary pyrrolidone dye vehicle in the patent. Thus, the patent discloses nonbiodegradable dye penetrant compositions wherein the volume of pyrrolidone employed as primary vehicle in the patent is essentially maintained minimal for the purpose of dissolving the dye.

Accordingly, an object of the present invention is the provision of an improved dye penetrant composition containing an extender which has a number of unique advantages over extenders previously employed in dye penetrant compositions. A particular object of the invention is the provision of a novel biodegradable dye penetrant composition containing a biodegradable extender which is relatively inexpensive and which is compatible with certain dye penetrant composition vehicles and with certain alloys used in aircraft construction such as titanium and nickel alloys, and particularly affording a biodegradable dye penetrant composition of extremely low volatility, low viscosity, low toxicity and which is substantially odorless. A further object is to provide an extended penetrant employing a non-volatile solvent which, since it does not evaporate, does not change the sensitivity and washability performance of the penetrant.

SUMMARY OF THE INVENTION

The above objects and advantages are achieved according to the invention by employing as an extender for a dye penetrant composition containing a biodegradable nonionic surfactant vehicle as defined in greater detail below, and a dye soluble therein, an N-lower alkyl 2-pyrrolidone having certain unique physical and chemical characteristics, as defined below. A particularly preferred extender of this type is N-methyl-2 pyrrolidone. The surfactant vehicles employed comprise particularly the aliphatic oxyalkylated alcohol surfactants disclosed in my above U.S. Pat. Nos. 3,915,885 and 3,915,886.

The above pyrrolidone solvent extender is particularly effective in conjunction with biodegradable nonionic surfactants employed as vehicle for the dye in the dye penetrant compositions hereof. The pyrrolidone solvent extender employed herein has a number of advantageous properties including low viscosity, low volatility, low flammability, no corrosive action on metals such as aluminum and titanium, low toxicity and absence of odor. Of particular importance, the solvent extender hereof is biodegradable, rendering the extended dye penetrant composition biodegradable, and such dye penetrant has extremely low viscosity. Thus, the biodegradable penetrant of the invention, thinned, for example, with N-methyl-2-pyrrolidone will have extremely low "drag out", and will be water thin, making the dye penetrant particularly useful and economical for application by two modes most commonly used for applying dye penetrant, namely, dipping and spraying.

In addition, dye penetrants obtained by employing the pyrrolidone hereof have the ability to quickly penetrate cracks and flaws, including microcracks, in parts, as described in greater detail hereinafter.

The liquid biodegradable dye penetrant compositions hereof including the above unique extender, and which does not evaporate as in the case of conventional extender solvents used commercially, can be formulated as a water washable or solvent removable dye penetrant composition containing a biodegradable nonionic water soluble surfactant, or as a post emulsifiable dye penetrant composition containing a biodegradable nonionic surfactant of relatively low solubility In the latter case, following application of the dye penetrant composition to the surface of an object to be inspected, an emulsifier composition is then applied to the surface, the emulsified penetrant composition is then removed as by spraying with water, and the surface inspected under suitable light to obtain the desired indications of cracks and other flaws in the part surface.

Thus, there is provided according to the invention a liquid dye penetrant composition for use in non-destructive testing for detecting cracks and other flaws in the surface of an object, comprising (1) a biodegradable nonionic surfactant consisting essentially of an oxyalkylated aliphatic alcohol or mixtures thereof, formed of an aliphatic primary or secondary alcohol carrying ethoxy or propoxy groups, or mixtures thereof, (2) a small amount of a dye soluble in said surfactant and (3) as extender, a substantial portion of an N-lower alkyl-2-pyrrolidone vehicle, especially N-methyl-2 pyrrolidone as defined more specifically hereinafter.

DETAILED DESCRIPTION OF EMBODIMENTS OF THE INVENTION

The nonionic surfactant or carrier, and which is employed essentially as the sole vehicle for the dye of the dye penetrant compositions according to the invention, includes certain preferably water soluble nonionic surfactants of low viscosity, which are compatible with the pyrrolidone solvent extender and the dye dissolved in the surfactant vehicle, and which are compatible with metals, particularly those employed in the aircraft industry, including aluminum, titanium and nickel alloys. Such nonionic surfactant must be capable of penetrating minute cracks and other defects in the surface of an object, to carry a film of dye penetrant composition into such cracks and other surface defects, so as to reveal such cracks and other defects due to the dye contained in the composition Suitable nonionic surfactant vehicles for the dye penetrant compositions of the invention are the oxyalkylated aliphatic alcohols which can be prepared by the reaction of an organic compound having a reactive hydrogen atom, such as an aliphatic alcohol, with ethylene oxide, propylene oxide, or mixtures thereof. Such surfactants are biodegradable.

Thus, the above nonionic surfactants consist essentially of an oxyalkylated aliphatic alcohol or mixtures thereof, formed of an aliphatic primary or secondary alcohol carrying ethoxy or propoxy groups, including polyoxyethylene or polyoxypropylene groups, or mixtures thereof.

More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One group of nonionic carriers within the class of materials defined immediately above is a cogeneric mixture of compounds represented by the formula:

R—O(A)H                                    (1)

wherein R is an essentially linear alkyl group having from 10 to 18 carbon atoms, with the priviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formuls, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetradecyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The above nonionic surfactants employed as carrier or vehicle for the dye of the penetrant solution according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12,75, and the number of propylene oxide groups in such mixture ranges from 1.7 to 7.0, the oxyethylene to oxypropylene ratio in such mixtures being from 1.8:1 to 2.2:1. This mixture of condensation products and the method of their preparation are disclosed in U.S. Pat. No. 3,340,309, and such disclosure is also incorporated herein by reference. The nonionic oxyalkylated alcohols marketed as the "RO-20" grades of "Plurafac", are believed representative of the class of surface active agents disclosed in the latter patent.

Various other "Plurafac" grades which are marketed and are believed to be generally within the above-described classes of oxyalkylated alcohol surfactants are those designated RA-43, A-24, A-25, B-25-5, B-26 and D-25.

Dye penetrant compositions containing the above described primary aliphatic oxyalkylated alcohols as vehicle, and a dye are described in my U.S. Pat. No. 3,915,885.

A class of particularly preferred nonionic biodegradable solvents or carriers which can be employed as substantially the sole vehicle for the dye of the dye penetrant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as carrier for the dye penetrant of the invention is a mixture of compounds which can be represented by the formula:

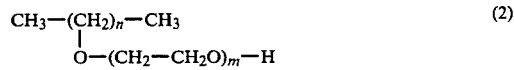

where n is in the range from 9 to 13, and m is 3 to 12.

Although preferably each of the above-defined surfactants is formed of a mixture of two or more linear alkyl hydrophobic chains ranging from $C_{11}$ to $C_{15}$, as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively, as:

Tergitol 15-S-3
Tergitol 15-S-5
Tergitol 15-S-7
Tergitol 15-S-9
Tergitol 15-S-12

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3; a mixture of 15-S-3 and 15-S-9; and a mixture of 15-S-5 and 15-S-9.

The above preferred class of nonionic biodegradable surfactants employed as carrier or vehicle for the dye of the penetrant solution according to the invention, are prepared by reacting an alcohol or mixture of alcohols, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above nonionic surfactants in the form of ethoxylates of linear secondary aliphatic alcohols, is described in U.S. Pat. No. 2,870,220.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility for production of dye penetrants having high sensitivity according to the invention, when employed in combination with the other water washable and water soluble Tergitols such as Tergitol 15-S-5 and Tergitol 15-S-9.

Dye penetrant compositions containing the above described ethoxylates of secondary aliphatic alcohols as vehicle and a dye are described in my U.S. Pat. No. 3,915,886.

Also, particularly effective dye penetrants are provided according to the invention employing a combination or mixture of the above Tergitols 15-S-5 and 15-S-9, and to which there can be added optionally Tergitol 15-S-3, as described in my U.S. Pat. No. 3,939,092.

There can also be employed ethoxylates of linear primary alcohols, corresponding to the ethoxylates of the linear secondary alcohols of the Tergitol S series of nonionic surfactants described above. Thus, the Tergitol 25-L series of nonionic surfactants is derived by ethoxylation of a blend of $C_{12}$ to $C_{15}$ linear primary alcohols, the soluble derivatives of which contain from about 5 to about 9 moles of ethylene oxide per mole of primary alcohol.

The extender incorporated into the dye penetrant composition of the invention containing a nonionic surfactant of the types exemplified above are the substituted lactams in the form of the N-alkyl-2-pyrrolidones, the alkyl group being a short carbon chain of not more than 4 carbon atoms. These pyrrolidones accordingly have the general formula:

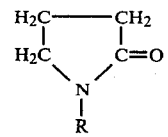

where R is an alkyl group containing from 1 to 4 carbon atoms. Examples of such groups are methyl, ethyl, propyl, isopropyl, butyl and isobutyl. Specific examples of these compounds are N-methyl-2pyrrolidone, N-ethyl-2-pyrrolidone, N-propyl-2-pyrrolidone, N-isopropyl-2-pyrrolidone, N-butyl-2-pyrrolidone, and N-isobutyl-2-pyrrolidone.

A particularly stable N-alkyl substituted pyrrolidone having the foregoing general structure and which is especially preferred in practicing the invention is N-methyl-2-pyrrolidone. Such pyrrolidone solvent has a freezing point of about <24° C. and a boiling point of 395° F., with a flash point of 204° F., and hence has extremely low volatility and is ideally suited for use as an extender in the dye penetrant disclosed herein. Moreover, it has a low viscosity of 1.65 centipoise at 25° C., which results in rapid and effective penetration of the penetrant containing such solvent extender in minute surface voids.

Since N-methyl-2-pyrrolidone is the preferred pyrrolidone extender according to the invention, the invention will be described hereinafter chiefly in terms of this specific pyrrolidone, although it will be understood that the other pyrrolidones described above also can be employed.

Thus, the N-methyl-2-pyrrolidone is nonflammable, non-toxic, noncorrosive to metals such as those noted above, and is highly water soluble and provides an excellent solvent for the above surfactants and dyes employed in the penetrant formulations of the invention. Of particular importance, it was unexpected to find that such pyrrolidone, in addition to functioning as an excellent solvent in the dye penetrant compositions employed, is substantially non-volatile and completely biodegradable, so that the resulting pyrrolidone extended dye penetrant containing the above biodegradable surfactants, is also biodegradable even when employing large volumes of the pyrrolidone extender therein. It was also unexpected to find that such pyrrolidone can be employed as an extender in the required volume, while the resulting penetrants still perform well and provide good dye indications at high dilution ratios. Also, such pyrrolidone is substantially completely miscible with each of the components of the dye penetrants hereof, thereby providing a substantially stable dye penetrant formulation wherein no precipitation of the dyes occurs.

Another important property of the pyrrolidone solvent extender of the invention is that it provides a quick penetration of cracks and other surface defects and a "creeping" of self-developing action in dye penetrants containing such solvent. By "creeping" or "self-developing action" is meant that the dye penetrant which penetrates into the cracks and other defects tends to exude therefrom without the aid of a developer, to provide colored indications of such cracks and other defects.

It is accordingly seen that the pyrrolidone extender employed in the dye penetrant compositions of the invention has a different function and is employed generally in substantially larger amounts than the pyrrolidone employed as the primary vehicle in my above U.S. Pat. No. 3,838,160. According to the latter patent, a nonbiodegradable dye penetrant is disclosed, wherein the volume of the primary pyrrolidone vehicle employed is only that necessary for the purpose of dissolving the dye, and is not employed as an extender therein, nor for the purposes of rendering the dye penetrant biodegradable.

Any suitable dye generally employed in dye penetrant compositions can be incorporated into the nonionic surfactants described above for producing the dye penetrant compositions employed in the invention process. Preferably, however, a fluorescent dye is employed for this purpose. The nonionic surfactant vehicle for the dye is compatible therewith and has the ability to dissolve either small or relatively large amounts of the dye and to hold a high concentration of dye in solution while providing good resolution and clarity of the dye trace in the cracks and other surface defects.

As previously noted, the dye penetrant solution employed according to the invention preferably contains a fluorescent dye. Various types of fluorescent dyes can be employed including for example the dye marketed as Fluorol 7GA Morton, Fluorescent Yellow G, and Hudson Yellow D 250, as well as other fluorescent dyes such as those marketed as Calcofluor Yellow, Azosol Brilliant Yellow 6GF, Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g. xyleneazo-beta-naphthol, Mefford No. 322 dye, believed to be o-toluene-azoxyleneazo-beta-naphthol, and the azo dyes marketed as Oil Red "O" and Sudan Red. Also, there can be employed to advantage the red-visible azo dyes disclosed in my U.S. Pat. No. 4,191,048 consisting essentially of an azo dye containing $C_5$–$C_{12}$ alkyl beta naphthols, or mixtures thereof, particularly containing $C_7H_{15}$ beta naphthols, such azo dye composition being a single phase liquid. A representative dye of this type is marketed as Automate Red, e.g. Automate Red "B". The disclosure of such patent is incorporated herein by reference. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The amount of dye which is incorporated into the nonionic, e.g. oxyalkylated alcohol, surfactant or carrier to produce the dye penetrant composition of the invention can vary, but can range generally from about 0.1 to 15, preferably about 0.5 to about 10, parts of the dye, or mixtures thereof, per 100 parts of such nonionic surfactant, by weight. In preparing the dye penetrant composition employed according to the invention, the dye can be added to the nonionic surfactant carrier in the desired proportion, and the pyrrolidone extender added to the mixed penetrant. The resulting dye penetrant composition has both high and low temprature stability.

The amount of pyrrolidone solvent extender added to the dye penetrant constitutes a substantial, and usually a major proportion, of the resulting solution, such solvent preferably being present in at least equal volumetric proportions with respect to the nonionic surfactant. Generally, the dye penetrant including the above nonionic surfactant and dye, is diluted with such solvent in a proportion ranging from about 0.5 to about 15, preferably about 1 to about 7, parts of the pyrrolidone solvent to 1 part dye penetrant, consisting of the sum of the other components, that is nonionic surfactant or surfactants, and dye, by volume.

Typical dye penetrant compositions to which the pyrrolidone solvent can be added according to the invention are as follows:

TABLE 1

| COMPONENTS | Compositions (Parts by Weight) | | | | | | | | |
| --- | --- | --- | --- | --- | --- | --- | --- | --- | --- |
| | A | B | C | D | E | F | G | H | I |
| Tergitol 15-S-5 | 75 | 75 | 50 | 100 | — | 75 | 75 | 75 | — |
| Tergitol 15-S-9 | 25 | 25 | — | — | 100 | 25 | 25 | 25 | — |
| Tergitol 15-S-3 | — | — | 50 | — | — | — | — | — | — |
| Plurafac A-24 | — | — | — | — | — | — | — | — | 100 |
| Calcofluor White RW | 5 | 2.5 | 5 | 5 | 2.5 | 1.5 | .75 | .375 | 1.5 |
| Fluorol 7 G A | 1.5 | .75 | 1.5 | 1.5 | .75 | — | — | — | — |
| Morton Fluorescent Yellow G | — | — | — | — | — | 0.5 | .25 | .125 | 0.5 |

As the volume of pyrrolidone extender solvent incorporated into the dye penetrant composition increases in relation to the nonionic surfactant and dye concentration, the level of dye penetrant sensitivity decreases, that is from high sensitivity employing a relatively low volume of pyrrolidone extender solvent, to low sensitivity employing a relatively high volume of pyrrolidone solvent. The pyrrolidone solvent can be introduced into the dye penetrant formulation at essentially any stage during the mixing and formulation of the dye penetrant.

Illustrative examples incorporating varying proportions of N-methyl-2-pyrrolione extender into the typical dye penetrant composition F of Table 1 above, and the sensitivity level of the resulting respective compositions, are set forth in Table 2 below.

TABLE 2

| Low-Viscosity Fluorescent Water Washable Penetrants | | | |
| --- | --- | --- | --- |
| DILUTED COMPO- SITIONS | DYE PENETRANT Composition F (Parts by Volume) | N—methyl-2- pyrrolidone Extender (Parts by Volume) | Approximate level of Penetrant Sensitivity Obtained |
| I | 1 | 1 | High Sensitivity |
| II | 1 | 2 | Medium Sensitivity |
| III | 1 | 6 | Low Sensitivity |

The following is an example of a typical biodegradable red-visible penetrant containing pyrrolidone extender according to the invention:

TABLE 3

| COMPOSITION J | |
| --- | --- |
| Components | Parts by Volume |
| Automate Red B (dye) | 1 |
| Surfactant Stock (Tergitol 15-S-5 (75%) and Tergitol 15-S-9 (25% by weight) | 14 |
| N—methyl-2-pyrrolidone | 10 |

The metal surfaces to which the dye penetrant compositions can be applied include a wide variety of metals and alloys and particularly those generally used in the aircraft industry, such as aluminum, copper, titanium, nickel, and their alloys, e.g. chromium plated brass, steel alloys such as PH14-8 Mo, the stainless series of steels, and the like.

If desired, a developer composition can be employed in conjunction with the pyrrolidone extender containing dye penetrant composition of the invention. When employed, a dry powder or non-aqueous (volatile solvent base) developer composition can be utilized. In each case, the developer composition contains a light colored powder, forming a coating which contrasts with the color of the dye in the penetrant and which acts as a wick or blotter, and causes liquid penetrant containing the dye, e.g. fluorescent dye, which was retained in the cracks or other surface flaws, to be drawn up out of such surface defects by capillary action and to "bleed" through the powder. Exemplary developer compositions for use in conjunction with the dye penetrant composition according to the invention, are those described in my U.S. Pat. No. 4,069,419, which is a dry powder developer consisting of fumed silica and talc, and in my U.S. Pat. No. 3,748,469, which is a wet non-aqueous developer composition consisting essentially of isopropyl alcohol, talc and glycol monobutyl ether. The description of such developer compositions contained in the above patents are incorporated herein by reference.

The dye penetrant composition employed in the invention process, utilizing the above nonionic, i.e. oxyalkylated alcohol, surfactants can be tailored to have varying degrees of sensitivity for detection of the smallest microcracks to gross cracks in a part surface by generally varying the amount of dye incorporated, and also be selecting particular surfactants or combinations thereof.

In the method for detecting cracks and other flaws in the surface of an object employing the pyrrolidone solvent extended dye penetrant composition of the invention, such dye penetrant is applied to the part surface in any suitable manner, as by spraying. The low viscosity solvent extended penetrant quickly penetrates surface defects such as the cracks in the part surface, and immediately after application of the dye penetrant to the surface of the test part, the excess dye penetrant composition is readily removed from the object surface by water washing, e.g. by application of a water spray or a sprayed mixture of air and water, or by wiping with a water moistened cloth. The solvent extended dye penetrant compositions hereof, particularly these containing the above Tergitols 15-S-5 to 15-S-9, generally have excellent wetability and practically instantaneous washability with water without removing dye penetrant from the cracks and defects on the part surface, followed by drying the part surface. The resulting solvent extended dye penetrant washed from the part surface is completely biodegradable. Such dye penetrant compositions can also be removed from the part surface by means, for example, of a volatile organic solvent such as an alcohol, e.g. isopropyl alcohol, a ketone such as acetone, or a chlorinated hydrocarbon such as trichlorethane. The solvent rapidly evaporates and the remaining pyrrolidone extended penetrant is biodegradable.

The pyrrolidone solvent extended dye penetrant of the invention has a self-developing action, in that such dye penetrant "creeps" or exudes from the cracks without the aid of a developer, to provide indications of the cracks when the part is thereafter viewed under suitable light, e.g. fluorescent light when the penetrant contains a fluorescent dye.

If desired, however, following removal of excess penetrant, a developer composition, eg. of the types noted above, can then be applied to the part surface followed by removal of excess developer, as by means of an air blast. The part is then viewed under suitable lighting conditions, employing black light or fluorescent illumination when the dye penetrant contains a fluorescent dye.

Where it is desired to employ a relatively water insoluble nonionic surfactant in the dye penetrant composition, such as Tergitol 15-S-3 noted above, alone or in substantial proportion in admixture with another water soluble Tergitol such as Tergitol 15-S-5, in order to obtain high sensitivity, the post emulsifiable dye penetrant inspection method of my U.S. Pat. No. 3,981,185 can be employed, According to such procedure, the dye penetrant composition containing the nonionic surfactant, e.g. the oxyalkylated alcohol nonionic surfactant, such as Tergitol 15-S-3 as carrier, and diluted with the pyrrolidone solvent according to the invention, can be applied as by dipping or spraying, preferably the latter, to a test part, followed by treatment of the penetrant covered part as by spraying, with an emulsifier containing as an essential component water soluble nonionic surfactants, e.g. nonionic surfactants of the same general class as employed as carrier for the dye in the dye penetrant composition, but having greater water solubility, such as Tergitol 15-S-9, or a combination of Tergitols 15-S-3 and 15-S-12. Water also can be added to the emulsifier. In such postemulsifiable process, the dye penetrant can contain an oxyalkylated alcohol nonionic surfactant according to formula (2) above, having an average value for m in such formula of about 3 to 4, and the oxyalkylated alcohol nonionic surfactant in the emulsifier can have an average value for m of about 5 to 12.

After a dwell time of about 1 to 5 minutes, the resulting emulsified penetrant is then removed from the surface of the part as by spraying with water, without dislodging the dye penetrant from the surface cracks and thus entrapping the penetrant therein, and the part surface is then dried and inspected under suitable light, e.g. ultraviolet light. The washed emulsified dye penetrant is completely biodegradable. If desired, a developer also can be employed following removal of the emulsified penetrant from the part surface.

The following is an example of a typical basic post emulsifiable dye penetrant composition having high sensitivity.

TABLE 4

| Composition K | |
|---|---|
| Components | Parts by weight |
| Tergitol 15-S-3 | 100 |
| Calcofluor White RW | 1.5 |
| Morton Fluorescent Yellow G | 0.5 |

Illustrative examples of post emulsifiable low viscosity fluorescent dye penetrants containing varying amounts of pyrrolidone solvent are set forth in Table 5 below.

TABLE 5
Biodegradable Fluorescent Post Emulsifiable Penetrants

| DILUTED COMPO-SITION | DYE PENETRANT COMPOSITION K (Parts by Volume) | N—methyl-2-pyrrolidone (Parts by Volume) | Approximate level of Penetrant Sensitivity Obtained |
| --- | --- | --- | --- |
| IV | 1 | 1 | High Sensitivity |
| V | 1 | 2 | Medium Sensitivity |
| VI | 1 | 6 | Low Sensitivity |

The above pyrrolidone solvent diluted penetrant compositions IV, V and VI of Table 5 can be employed in conjunction with a subsequent emulsifier solution such as illustrated in Table 6 below:

TABLE 6
COMPOSITION L

| Components | Parts by Volume |
| --- | --- |
| Tergitol 15-S-3 | 15 |
| Tergitol 15-S-12 | 50 |
| Water Distilled | 390 |

If desired, a small amount of dye such as Rhodanine can be used to color the emulsifier in order to impart visibility to the solution.

The following are examples of practice of the invention.

EXAMPLE 1

The low viscosity diluted pyrrolidone solvent extended composition I of Table 2 above was applied as by spraying, to one-half of the surface of a cracked aluminum test panel containing minute cracks of the order of 0.001" to 0.0001" in width, closely distributed over the entire surface. A water wash was then applied as by an air-water spray over the coating of the dye penetrant composition I on the test panel, causing instantaneous washing away of the dye penetrant on the surface cracks and thus entrapping the penetrant therein. The washed dye penetrant composition I was completely biodegradable.

The other half of the test panel surface was sprayed with the undiluted dye penetrant composition F of Table 1 above, and which was the basic composition employed in producing the diluted pyrrolidone solvent-containing dye penetrant composition I of the invention, and utilized on the first half of the test panel. A water wash was then applied by an air-water spray over the coating of the dye penetrant composition F to wash away excess dye penetrant from the surface of the panel.

Both halves of the test panel surface to which the diluted dye penetrant composition I above and dye penetrant composition F were initially respectively applied, were then covered with the powder developer below, disclosed in my U.S. Pat. No. 4,069,419.

TABLE 7

| Components | % by Weight |
| --- | --- |
| Talc | 50 |
| Fumed Silica | 50 |

The above developer was permitted to dwell over the two half surfaces of the test panel for a period of about 2 minutes.

Excess developer composition was then carefully removed from both half surfaces of the test panel by means of a gentle air blast.

The panel was then placed under black light (fluorescent) illumination and the respective half surfaces viewed in such illumination. It was observed that the first half side of the panel which was initially treated with diluted dye penetrant composition I according to the invention, disclosed fluorescent indications from numerous readily defined microcracks, which fluorescent indications were substantially of the same brightness and concentration as those fluorescent indications from the microcracks on the half side of the panel which had been initially treated with the basic penetrant composition F.

EXAMPLE 2

Tests on chromium panels containing microcracks were carried out employing procedures similar to that employed in Example 1, utilizing composition II of Table 2, the medium sensitivity low viscosity diluted fluorescent dye penetrant composition of the invention on one-half of the surface the test panel and utilizing the basic medium sensitivity undiluted basic composition G of Table 1 on the other half of the panel.

Results obtained were similar to those obtained in Example 1, except that in both cases the sensitivity and concentration of cracks revealed were not as great as for the high sensitivity dye penetrant compositions I and F of Example 1.

EXAMPLE 3

The high sensitivity low viscosity post emulsifiable penetrant composition IV of Table 5 above was applied as by spraying to one-half of the surface of an aluminum test panel containing microcracks.

The other half of the test panel surface was sprayed with the undiluted high sensitivity post emulsifiable dye penetrant composition K of Table 4.

The dye penetrant covered surfaces on both halves of the test panel were then sprayed with the emulsifier solution composition L of Table 6 above, the emulsifier being allowed to dwell on the initially applied penetrant for about 2 minutes, and thereafter a spray of water was used to remove the emulsifier-penetrant blend on each half of the panel.

Both halves of the test panel were then covered with the powder developer of Table 7 above and excess developer composition was then removed from both surfaces of the test panel by means of a gentle air blast.

The panel was then placed under black light (fluorescent) illumination and the above treated surfaces on both halves of the panel viewed in such illumination. The sharpness and brilliance of the fluorescent indications on the first half of the panel to which the pyrrolidone solvent diluted post emulsifiable penetrant was applied were substantially the same as for the other half of the panel to which the undiluted post emulsifiable penetrant was applied.

EXAMPLE 4

The procedure of Example 1 was followed except that the first half of the panel was treated initially with a low viscosity red-visible water washable dye penetrant composition J of Table 3 above and the other half of the panel was treated with the same dye penetrant composition but which was not diluted with the pyrrolidone solvent.

Both halves of the test panel, following developing according to Example 1, were viewed in visible light, revealing visual colored traces of crack indications on both sides of the panel of approximately equal brightness and intensity.

EXAMPLE 5

The penetrant solution composition I of Table 2 containing the pyrrolidone extender was applied to aluminum metal specimens and some of such specimens were submitted to a prolonged period of about 3 hours to heat and hot air currents at about 150° to 160° F. inside an air circulating type oven.

The specimens so heated were removed from the oven, cooled to room temperature and washed with water, and showed no difference in washability of the dye penetrant as compared to washability of the same aluminum specimens containing the same dye penetrant and which were not subjected to the above heating test.

This indicates that the pyrrolidone extender did not evaporate from the penetrant containing specimens that were heated, and that such pyrrolidone is essentially non-volatile under dye penetrant inspection conditions at relatively high temperatures.

Prior to applying the developer in the tests of the above Examples 1 to 4, observations were made on the half portions of the test panels covered with the three types of low viscosity solvent extended dye penetrants of the invention, namely, the low viscosity fluorescent water washable penetrant composition I of Table 2, the low viscosity fluorescent post emulsifiable penetrant composition IV of Table 5, and the low viscosity red-visible water washable penetrant of Example 4, to judge their self-developing action produced by utilizing the pyrrolidone solvent. In all cases these penetrants appeared to have remarkable self-developing action in that the dye penetrant appeared to commence exuding from the cracks shortly after removal of excess dye penetrant from the part surfaces. This unique property of the dye penetrant obtained using the biodegradable pyrrolidone solvent of the invention appears related to the low viscosity and quick penetration of the resulting dye penetrant into the surface cracks. The low viscosity of the dye penetrant also results in reduced drag-out action, namely, the ability of the dye penetrant to readily drip from the part. Thus, when carrying out the dye penetrant process employing a dye penetrant tank, as by dipping the parts in the tank, such quick drainage of excess dye penetrant from the part when it is removed from the tank permits recovery of excess penetrant and thus increases the economy of the system.

The excess of both pyrrolidone extended water washable dye penetrants of the invention, e.g. compositions I of Example 1 and J of Example 4, and the pyrrolidone solvent extended post emulsifiable dye penetrant compositions of the invention, e.g. composition IV of Example 3, following emulsification thereof, also can be removed from a part surface by washing with isopropyl alcohol or trichlorothane instead of with water. The solvent rapidly evaporates, rendering the resulting composition biodegradable.

All of the pyrrolidone solvent diluted formulations of the examples appeared stable and no odor therefrom was detected. Washability of the water-washable diluted dye penetrants from the parts was excellent, yet no overwashing of penetrant from the defects or cracks in the test samples occurred during the tests.

From the foregoing, it is seen that the invention provides a highly effective water washable, solvent removable or post emulsifiable biodegradable dye penetrant composition consisting essentially of an oxyalkylated aliphatic alcohol biodegradable nonionic surfactant and a dye, which is preferably fluorescent, and including a unique biodegradable extender in the form of an N-alkyl-2-pyrrolidone, particularly N-methyl-2-pyrrolidone solvent having very low volatility. Application of such pyrrolidone solvent extended dye penetrant compositions to a part surface for detection of cracks therein results in efficiently and quickly obtaining fluorescent or visible light indications of cracks in the part surface, equivalent in this respect to the results obtained employing the same basic dye penetrant but in the absence of the pyrrolidone solvent extender.

Since various changes and modifications of the invention will occur to and can be made readily by those skilled in the art without departing from the invention concept, the invention is not to be taken as limited except by the scope of the appended claims.

I claim:

1. A biodegradable liquid dye penetrant composition for use in nondestructive testing for detecting cracks and other defects in the surface of an object, comprising (1) a nonionic surfactant consisting essentially of an oxyalkylated aliphatic alcohol or mixtures thereof, formed of an aliphatic primary or secondary alcohol carrying ethoxy or propoxy groups, or mixtures thereof (2) a small amount of a dye soluble in said surfactant and (3) as extender, a substantial portion of an N-alkyl-2-pyrrolidone having the general formula:

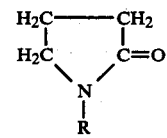

where R is an alkyl group containing from 1 to 4 carbon atoms.

2. The dye penetrant composition as defined in claim 1, said pyrrolidone extender being N-methyl-2-pyrrolidone.

3. The dye penetrant composition as defined in claim 2, said nonionic surfactant being of the group consisting of (a) straight chain, primary, aliphatic oxyalkylated alcohols, wherein said alcohols can contain from 8 to 20 carbon atoms and the oxyalkyl groups are ethylene oxide, propylene oxide, or a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide.

4. The dye penetrant composition as defined in claim 3, wherein said nonionic surfactant in the dye penetrant composition is the sole liquid carrier for the dye therein.

5. The dye penetrant composition as defined in claim 3, wherein said surfactant (a) is a mixture of compounds having the formula:

R—O(A)H wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) are ethoxylates of a mixture of alcohols having the formula:

$$CH_3-(CH_2)_n-CH_3$$
$$|$$
$$O-(CH_2-CH_2O)_m-H$$

where n is in the range from 9 to 13 and m is an average of 3 to 12; and said dye is present in said composition in an amount ranging from about 0.1 to 15 parts, per 100 parts, by weight, of said surfactant.

6. The dye penetrant composition as defined in claim 5, wherein R in said surfactant (a) can have from 12 to 18 carbon atoms, and the total number of A groups can range from about 4 to about 14; and wherein in said surfactant (b) the linear alkyl hydrophobic portion of said surfactant is a polyoxyethylene chain randomly attached to the linear alkyl hydrophobic chains through an ether linkage, and wherein said surfactant (b) is selected from the group consisting of said ethoxylates of said mixture of alcohols, wherein n ranges from 9 to 13, and m is an average of 3, 5, 7, 9 or 12.

7. The dye penetrant composition as defined in claim 2, wherein said dye is a fluorescent dye.

8. The dye penetrant composition as defined in claim 2, wherein said dye is a red-visible azo dye composition containing $C_5$-$C_{12}$ alkyl beta naphthols, or mixtures thereof.

9. The dye penetrant composition as defined in claim 2, wherein said surfactant consists of ethoxylates of a mixture of alcohols having the formula:

$$CH_3-(CH_2)_n-CH_3$$
$$|$$
$$O-(CH_2-CH_2O)_m-H$$

where n is in the range from 9 to 13 and m is an average of 3 to 12.

10. The dye penetrant composition as defined in claim 9, wherein said surfactant is selected from the group consisting of said ethoxylates of said mixture of alcohols wherein n ranges from 9 to 13, and m is an average of 3, 5, 7, 9, or 12.

11. The dye penetrant composition as defined in claim 9, wherein said dye is a fluorescent dye, said solvent being present in at least equal volumetric proportions with respect to said surfactant.

12. The dye penetrant composition as defined in claim 2, wherein said surfactant consists of the ethoxylates of a mixture of $C_{12}$ to $C_{15}$ linear primary alcohols and contains from 5 to 9 moles of ethylene oxide per mole of primary alcohol.

13. The dye penetrant composition as defined in claim 2, said pyrrolidone solvent being present in an amount ranging from about 0.5 to 15 parts, to 1 part of the sum of said surfactant and said dye, by volume.

14. The dye penetrant composition as defined in claim 2, said pyrrolidone being present in an amount ranging from about 1 to 7 parts, to 1 part of the sum of said surfactant and said dye, by volume.

15. The dye penetrant composition as defined in claim 9, said pyrrolidone being present in an amount ranging from about 1 to 7 parts, to 1 part of the sum of said surfactant and said dye, by volume.

16. The dye penetrant composition as defined in claim 9, employing a combination of said nonionic surfactants wherein m in one of said surfactants is an average of 5 and m in another of said surfactants is an average of 9.

17. The dye penetrant composition as defined in claim 16, wherein said dye is a fluorescent dye and said dye is present in said composition in an amount ranging from about 0.1 to 15 parts, per 100 parts, by weight of said surfactant, said pyrrolidone solvent being present in an amount ranging from about 1 to 7 parts, to 1 part of the sum of said surfactant and said dye, by volume.

* * * * *